(12) United States Patent
Tope et al.

(10) Patent No.: US 12,351,763 B2
(45) Date of Patent: Jul. 8, 2025

(54) METHODS, APPARATUSES, AND SYSTEMS FOR CONVERSION OF BIOETHANOL TO RENEWABLE JET FUEL

(71) Applicant: Honeywell International Inc., Charlotte, NC (US)

(72) Inventors: Balkrishna Tope, Pune (IN); Vikrant Vilasrao Dalal, Gurgaon (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 189 days.

(21) Appl. No.: 18/350,386

(22) Filed: Jul. 11, 2023

(65) Prior Publication Data

US 2025/0019603 A1   Jan. 16, 2025

(51) Int. Cl.
*C10G 65/04* (2006.01)
*C07C 1/24* (2006.01)
(Continued)

(52) U.S. Cl.
CPC .............. *C10G 65/043* (2013.01); *C07C 1/24* (2013.01); *C07C 2/06* (2013.01); *C07C 5/02* (2013.01); *C07C 5/03* (2013.01); *C07C 5/09* (2013.01); *C07C 11/04* (2013.01); *C07C 31/08* (2013.01); *C10G 45/58* (2013.01); *C10G 50/00* (2013.01); *C10L 1/08* (2013.01); *C10L 10/14* (2013.01); *C07C 2521/04* (2013.01); *C10G 2300/1088* (2013.01); *C10G 2300/4037* (2013.01);
(Continued)

(58) Field of Classification Search
CPC ...... C10G 65/043; C10G 45/58; C10G 50/00; C10G 2300/1088; C10G 2300/4037; C10G 2300/4081; C10G 2400/08; C07C 1/24; C07C 2/06; C07C 5/02; C07C 5/03; C07C 5/09; C07C 11/04; C07C 31/08; C07C 2521/04; C10L 1/08; C10L 10/14; C10L 2290/60; Y02P 30/20
See application file for complete search history.

(56) References Cited

U.S. PATENT DOCUMENTS

2009/0287029 A1* 11/2009 Anumakonda ........ C10G 45/64
585/16
2013/0305591 A1* 11/2013 McCall .................... C10L 1/08
585/240
(Continued)

*Primary Examiner* — Ali Z Fadhel
(74) *Attorney, Agent, or Firm* — Alston & Bird LLP

(57) ABSTRACT

Methods, apparatuses, and systems for the conversion of bioethanol to renewable jet fuel are disclosed. In an example embodiment, a method for converting bioethanol to renewable jet fuel includes providing an olefin process stream comprising olefins to a hydrogenation reaction zone, converting at least a portion of the olefin process stream to a product stream comprising jet-range compatible hydrocarbons, determining, in the hydrogenation reaction zone, an iso-to-normal ratio of a portion of the product stream via one or more online analyzers, in an instance wherein the determined iso-to-normal ratio fails to satisfy a predetermined iso-to-normal threshold ratio, determine at least one additive and an amount of the at least one additive to be added to the product stream, the at least one additive configured to adjust a freeze point of the product stream, and adding the at least one additive to the product stream prior to the product stream exiting the hydrogenation reaction zone.

20 Claims, 5 Drawing Sheets

(51) Int. Cl.
*C07C 2/06* (2006.01)
*C07C 5/02* (2006.01)
*C07C 5/03* (2006.01)
*C07C 5/09* (2006.01)
*C07C 11/04* (2006.01)
*C07C 31/08* (2006.01)
*C10G 45/58* (2006.01)
*C10G 50/00* (2006.01)
*C10L 1/08* (2006.01)
*C10L 10/14* (2006.01)

(52) U.S. Cl.
CPC . *C10G 2300/4081* (2013.01); *C10G 2400/08* (2013.01); *C10L 2290/60* (2013.01)

(56) References Cited

U.S. PATENT DOCUMENTS

| | | | |
|---|---|---|---|
| 2023/0098592 A1* | 3/2023 | Novak | C10G 35/065 585/240 |
| 2024/0124792 A1* | 4/2024 | Zhou | B01J 37/18 |

* cited by examiner

METHODS, APPARATUSES, AND SYSTEMS FOR CONVERSION OF BIOETHANOL TO RENEWABLE JET FUEL

TECHNOLOGICAL FIELD

Example embodiments of the present disclosure relate generally to aviation fuel and, more particularly, to methods, apparatuses, and systems for the conversion of bioethanol to renewable jet fuel.

BACKGROUND

The aviation sector has come under increasing pressure to decrease its carbon emissions. Indeed, certain governmental policies may require or reward use of biorenewable-sourced jet fuel or sustainable aviation fuel (SAF) blending in order to decrease such carbon or greenhouse gas emissions. For example, the U.S. government announced the Sustainable Aviation Fuel Grand Challenge in 2021, setting a goal for, inter alia, SAF to meet 100% of aviation fuel demand by 2050. Similarly, the Indian government has promoted surplus ethanol blending with conventional aviation fuel to foster a circular bio-economy that replaces non-renewable, fossil-based products.

Applicant has identified a number of deficiencies and problems associated with conventional jet fuel and conventional technologies for converting biorenewable sources to renewable or "green" jet fuel. Through applied effort, ingenuity, and innovation, many of these identified problems have been solved by developing solutions that are included in embodiments of the present disclosure, many examples of which are described in detail herein.

BRIEF SUMMARY

In general, example embodiments of the present disclosure provided herein may provide solutions to the problems and needs in the art that have not yet been fully identified, appreciated, or solved by current technologies for converting biorenewable sources to renewable or "green" jet fuel. In accordance with one exemplary embodiment of the present disclosure, a method for converting bioethanol to renewable jet fuel is disclosed, the method including hydrogenating, in a hydrogenation reaction zone, at least a portion of an olefin process stream comprising olefins to produce a product stream comprising jet-range compatible hydrocarbons, wherein the olefins are formed from bioethanol; determining, in the hydrogenation reaction zone, an iso-to-normal ratio of a portion of the product stream via one or more online analyzers; in an instance wherein the determined iso-to-normal ratio fails to satisfy a predetermined iso-to-normal threshold ratio, determine at least one additive and an amount of the at least one additive to be added to the product stream, the at least one additive configured to adjust a freeze point of the product stream; and adding the at least one additive to the product stream prior to the product stream exiting the hydrogenation reaction zone.

In some embodiments, at least one of the one or more online analyzers is configured to determine the iso-to-normal ratio of the portion of the product stream in real time. In other embodiments, the one or more online analyzers comprise one or more sensors configured to continuously and/or intermittently monitor the iso-to-normal ratio of the product stream.

In some embodiments, the one or more online analyzers are configured to communicate with a controller, the controller configured to add the least one additive to the product stream.

In some embodiments, the predetermined iso-to-normal threshold ratio is correlated to a freeze point specification dictated by ASTM D7566. In certain embodiments, the predetermined iso-to-normal threshold ratio is at least 14:1.

In some embodiments, the method further includes providing bioethanol to a dehydration reaction zone; and dehydrating at least a portion of the bioethanol to produce an ethylene process stream comprising ethylene. In certain embodiments, dehydrating at least a portion of the bioethanol is performed in the presence of a dehydration catalyst. In still further embodiments, the dehydration catalyst is gamma alumina.

In some embodiments, the method further includes providing the ethylene process stream to an oligomerization reaction zone; and oligomerizing at least a portion of the ethylene process stream to produce the olefin process stream. In certain embodiments, the method further includes removing lighter olefins having less than nine carbon atoms from the olefin process stream. In still further embodiments, the method includes recycling the removed lighter olefins back into the oligomerization reaction zone.

In accordance with another exemplary embodiment of the present disclosure, a system configured to convert bioethanol to renewable jet fuel is disclosed, the system including a hydrogenation reaction zone configured to produce a product stream comprising jet-range compatible hydrocarbons; one or more online analyzers, wherein each online analyzer is configured to determine an iso-to-normal ratio of a portion of the product stream in the hydrogenation reaction zone; and a controller communicably coupled to the one or more online analyzers, wherein the controller is configured to in an instance wherein the determined iso-to-normal ratio fails to satisfy a predetermined iso-to-normal threshold ratio, determine at least one additive and an amount of the at least one additive to be added to the product stream, the at least one additive configured to adjust a freeze point of the product stream, and add the at least one additive to the product stream prior to the product stream exiting the hydrogenation reaction zone.

In some embodiments, the predetermined iso-to-normal threshold ratio is at least 14:1.

In some embodiments, the hydrogenation reaction zone is configured to receive an olefin process stream comprising olefins; and hydrogenate at least a portion of the olefin process stream to produce the product stream comprising jet-range compatible hydrocarbons. In certain embodiments, the system further includes a dehydration reaction zone disposed upstream of the hydrogenation reaction zone, the dehydration reaction zone configured to: receive a starting material stream comprising bioethanol; and dehydrate, in the presence of a dehydration catalyst, at least a portion of the starting material stream to produce an ethylene process stream comprising ethylene. In still further embodiments, the system further includes an oligomerization reaction zone disposed upstream of the hydrogenation reaction zone and downstream of the dehydration reaction zone, the oligomerization reaction zone configured to: receive the ethylene process stream; and oligomerize, in the presence of an oligomerization catalyst, at least a portion of the ethylene process stream to produce the olefin process stream.

In some embodiments, the system is configured to remove at least a portion of lighter olefins from the olefin process stream, the lighter olefins having less than nine carbon atoms. In still further embodiments, the system is configured to recycle the removed lighter olefins back into the oligomerization reaction zone.

In some embodiments, the one or more online analyzers each comprise one or more sensors configured to continuously and/or intermittently monitor the iso-to-normal ratio of the product stream.

BRIEF DESCRIPTION OF THE DRAWINGS

Having thus described the present disclosure in general terms, reference will now be made to the accompanying drawings, which are not necessarily drawn to scale. The components illustrated in the figures may or may not be present in certain embodiments described herein. Some embodiments may include fewer (or more) components than those shown in the figures.

Figure 1:
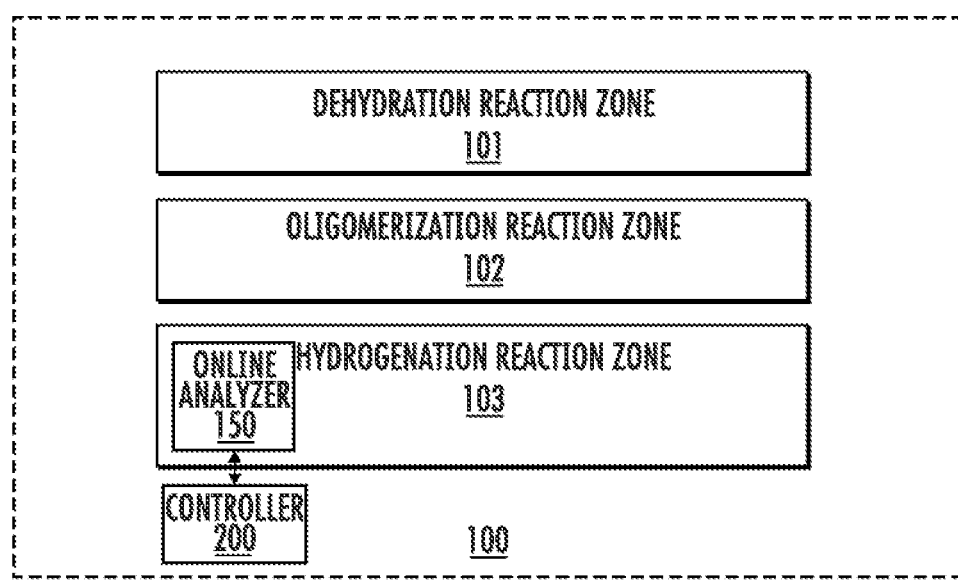

FIG. 1 illustrates a schematic representation of a system in accordance with some example embodiments described herein.

Figure 2:
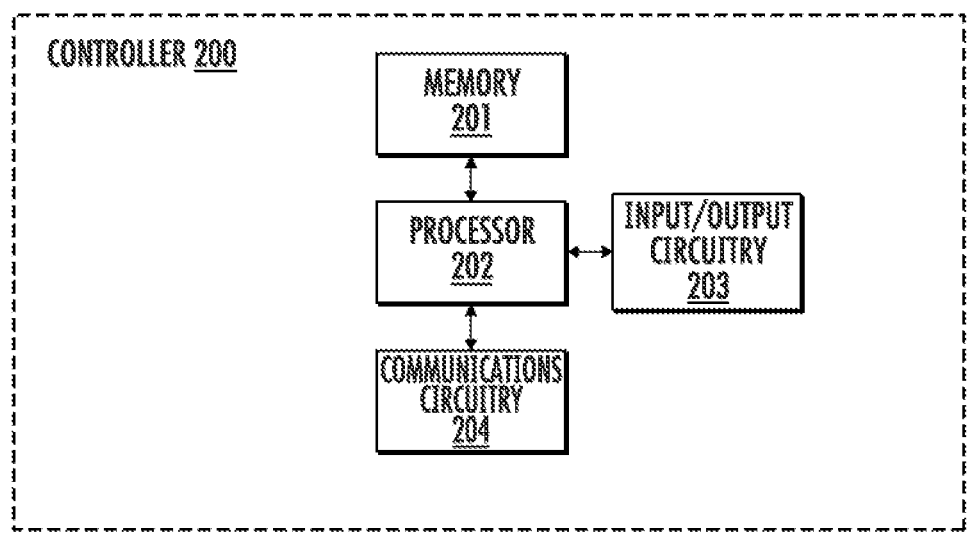

FIG. 2 illustrates a schematic block diagram of example circuitry that may perform various operations, in accordance with some example embodiments described herein.

Figure 3:
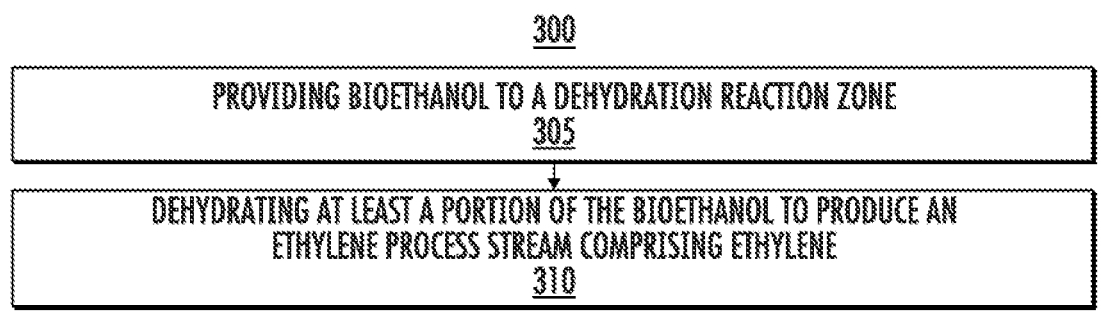

FIG. 3 illustrates an example flowchart for dehydrating bioethanol in a dehydration reaction zone in accordance with some example embodiments described herein.

Figure 4:
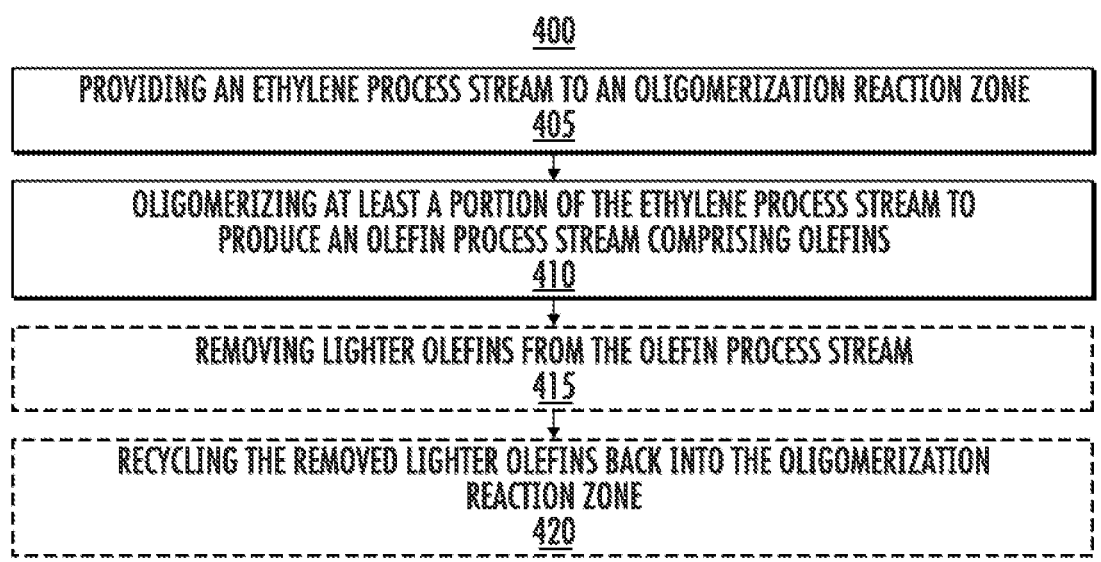

FIG. 4 illustrates an example flowchart for oligomerizing ethylene in a oligomerization reaction zone in accordance with some example embodiments described herein.

Figure 5:
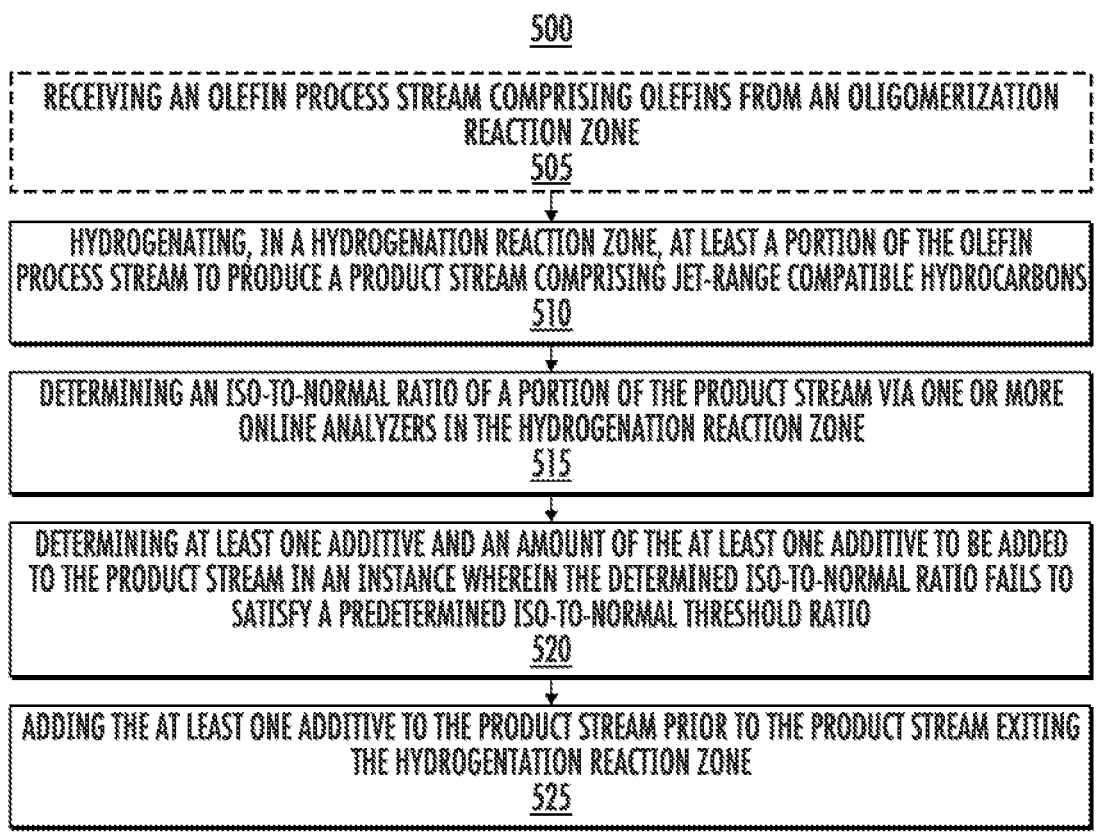

FIG. 5 illustrates an example flowchart for hydrogenating an oligomer process stream in a hydrogenation reaction zone in accordance with some example embodiments described herein.

OVERVIEW

SAF, or low-carbon sustainable aviation fuel prepared from biorenewable sources (i.e., non-petroleum feedstocks), has similar properties to conventional jet fuel but has a smaller carbon footprint and does not require any changes to aircraft technology or associated fuel infrastructure. In some instances, SAF may also be mixed with conventional fossil fuel-based jet fuel in order to reduce carbon emissions as well as the demand for the extraction and use of fossil fuels. For example, surplus bioethanol or ethyl alcohol blending may reduce dependency on imported crude oil and otherwise reduce or minimize the carbon footprint and promote carbon neutrality in the fuel sector.

Various embodiments of the present disclosure provide methods, apparatuses, and systems for the conversion of bioethanol to renewable jet fuel. Bioethanol or cellulosic ethanol is an alcohol which can be made by fermenting plant-based carbohydrates. Bioethanol may be categorized as first (1G), second (2G), or third (3G) generation, based on the source of the materials used to manufacture the bioethanol. For example, 1G bioethanol may be produced from sugar- or starch-based edible feedstocks, such as corn seeds, sugar cane, and grains, 2G bioethanol may be produced from waste products (e.g., to avoid a food versus fuel dilemma), such as the inedible byproducts of food crops after harvest (e.g., rice husks, corn cobs, etc.), and 3G bioethanol may be produced by algae from waste water, sewage, or salt water.

The inventors have determined it would be desirable and advantageous to be able to efficiently convert such bioethanol, regardless of source, to renewable jet fuel in a commercial process, such that the hydrocarbon product of such process satisfies the various specifications as dictated by ASTM D7566, "Standard Specification for Aviation Turbine Fuel Containing Synthesized Hydrocarbons". That is, embodiments of the present disclosure may provide a high conversion and excellent selectively to jet fuel-compatible hydrocarbons (e.g., C9+ hydrocarbons) such that the hydrocarbon product, inter alia, boils in the conventional jet fuel range and meets the density at 15 deg C. threshold specification of ASTM D7566 of 770 kg/m$^3$. Such high conversion and excellent selectively to jet fuel-compatible hydrocarbons in turn promotes a circular bio-economy, facilitates a reduced carbon footprint (e.g., may reduce greenhouse gas emissions by 80% on a total lifecycle basis), encourages carbon credits, provides a boost to local agricultural sectors (e.g. in order to sustainably produce the base feedstocks at a large scale), enables a lower CAPEX and OPEX, and otherwise reduces cost expenditures typically incurred in manufacturing such biorenewables.

Example embodiments of the present disclosure may convert bioethanol to jet fuel-compatible hydrocarbons via a series of steps, including dehydration, oligomerization, and mild hydrogenation. For example, in some embodiments, bioethanol ($C_2H_5OH$) may be converted to ethylene ($C_2H_4$) via a dehydration step. Bioethanol may contain a substantial amount of water (e.g., almost 40%) and it may be necessary to reduce the amount of such water in order to efficiently convert the bioethanol. In some embodiments, a dehydration catalyst, such as gamma alumina, is used in the dehydration step.

In another example embodiment, the resulting ethylene may be oligomerized over an oligomerization catalyst into longer carbon chain olefins via an oligomerization step. The inventors have determined it may be undesirable to include a separate dimerization step prior to such oligomerization step (e.g., dimerize ethylene to butylene ($C_4H_8$) and then subject such butylene to an oligomerization step). Rather, it may be advantageous to not include a separate dimerization step in order to lower CAPEX and OPEX associated with the system, and additionally or alternatively, selectively utilize an oligomerization catalyst such that either dimerization is not required or very minimal dimerization occurs, for example, in a single reactor system.

Additionally or alternatively, in some embodiments, lighter olefins that have not formed at least C9-C14 hydrocarbons are removed from the system and/or recycled back into the oligomerization portion in order to be further oligomerized into jet fuel-compatible range and further maximize the conversion toward jet fuel-compatible hydrocarbons (e.g., predominantly C9-C14 jet range components).

In still another example embodiment, the longer carbon chain olefins may be subjected to a mild hydrogenation process in order to saturate the olefinic components. ASTM D7566 further dictates certain cold flow properties for SAF, such as freezing point and flash specifications. The inventors have determined that it would be desirable and advantageous to have a higher iso-to-normal ratio (e.g., 14:1, 15:1, etc.) of the C9-C14 hydrocarbon product as such a product may confidently result in cold flow properties that necessarily meet or satisfy at least the freezing point specifications dictated by ASTM D7566. Accordingly, the hydrogenation step may be structured to maximize isomerization (e.g., selected hydrogenation catalyst) and further increase an iso-to-normal ratio of the C9-C14 hydrocarbons in order to enhance cold flow properties of the SAF.

Applicants have determined that it is undesirable to discover, after completion of an SAF batch, that an entire SAF batch may be "off spec" such that it fails to meet the necessary SAF freeze point specifications. In order to compensate for such "off spec" batches, it may be necessary to add large amounts of additives, which are cost-prohibitive, in an attempt to correct that particular batch. Accordingly, the inventors have determined it would be desirable and advantageous to incorporate one or more online analyzers in order to monitor the freeze point requirements, in real time, during a commercial process for converting bioethanol to green fuel or SAF. Although example embodiments of the present disclosure may demonstrate an excellent selectivity to the formation of C9-C14 iso-alkanes, example embodiments of the present disclosure may additionally or alternatively incorporate an online analyzer to monitor and/or calculate a freeze point value based on the iso-to-normal ratio of the C9-C14 hydrocarbon jet range components to be used as a positive feedback control loop in order to continually refine and selectively adjust the addition of one or more external additives during a commercial bioethanol conversion process. That is, some embodiments of the present disclosure are able to advantageously and more accurately determine, speciate, and/or quantify C9-C14 iso-alkanes at the molecular level and in real time, and correlate such molecular level information to calculate a predicted freeze point value of the material and thereby adjust accordingly, if necessary, via selective and controlled addition of additives. In other words, the inventors have determined it would be desirable and advantageous to use such feedback control loop to confidently achieve the SAF freeze point specifications as dictated by ASTM D7566, reduce resource expenditure, and maximize production efficiency. For example, end users such as airlines, airport authorities, or SAF aggregators, may obtain maximum benefits of carbon reduction by being able to confidently blend such renewable jet fuel up to maximum blending limits, depending on the source of the bio-feedstock.

These characteristics as well as additional features, functions, and details are described below. Similarly, corresponding and additional embodiments are also described below.

DETAILED DESCRIPTION

Embodiments of the present disclosure now will be described more fully hereinafter with reference to the accompanying drawings. It should be understood that some, but not all embodiments are shown and described herein. Indeed, the embodiments may take many different forms, and accordingly, this disclosure should not be construed as limited to the embodiments set forth herein. Rather, these embodiments are provided so that this disclosure will satisfy applicable legal requirements. Like numbers refer to like elements throughout.

Example Systems and Apparatuses of the Disclosure

With reference to FIG. 1, an example system 100 according to one example embodiment is illustrated. In some embodiments, the system 100 may comprise a single reactor with one or more reaction zones. For example, in one embodiment, the system 100 comprises a single reactor comprising at least a dehydration reaction zone 101, an oligomerization reaction zone 102, and a hydrogenation reaction zone 103. In some embodiments, the dehydration reaction zone 101 is disposed upstream of the oligomerization reaction zone 102 and the oligomerization reaction zone 102 is disposed upstream of the hydrogenation reaction zone 103. In other embodiments, two or more of the reactions zones are the same reaction zone. In other words, the reaction zones may be overlapping or separated.

In other embodiments, the system 100 comprises two or more reactors, each reactor having one or more reaction zones. In a non-limiting example, the system 100 comprises a first reactor comprising the dehydration reaction zone 101, a second reactor comprising the oligomerization reaction zone 102, and third reactor comprising the hydrogenation reaction zone 103. The reactors may appropriately be interconnected to provide a continuous process.

With continued reference to FIG. 1, in some embodiments, the system 100 comprises one or more online analyzers 200. The online analyzer(s) 150 may enable in-line optimization of the freezing point of the corresponding material. For example, an example online analyzer 150 may include one or more sensors or probes configured to be placed or disposed within the reaction medium and/or product stream of the hydrogenation reaction zone.

In some embodiments, the online analyzer(s) 150 are configured to determine the iso-to-normal ratio of a portion of the product stream (e.g., in the hydrogenation reaction zone). For example, as described herein, the product stream in the hydrogenation reaction zone 103 comprises jet-range compatible hydrocarbons (i.e., saturated C9-C14 alkanes). The sensor(s) or probe(s) of the online analyzer(s) 150 are disposed within the product stream in the hydrogenation reaction zone 103 and are configured to detect and/or speciate the alkanes at the molecular level to determine the iso-to-normal ratio of the hydrocarbons in the product stream. For example, in some embodiments, the online analyzer(s) 150 quantify the iso-alkanes versus the n-alkanes at the molecular level and correlate such molecular level information to a predicted freeze point value of the product material. As described herein, the inventors have determined that it is desirable and advantageous to have a higher iso-to-normal ratio, such as at least 14:1, to be able to confidently obtain, meet, and/or satisfy the cold flow properties dictated by ASTM D7566.

In some embodiments, the online analyzer(s) 150 determine the iso-to-normal ratio of the product stream in real time. In still other embodiments, the sensor(s) or probe(s) of the online analyzer(s) 150 continuously and/or intermittently monitor the iso-to-normal ratio of the product stream. For example, in some embodiments, a sensor may collect data to determine the iso-to-normal ratio at intervals of about 1 second, about 2 seconds, about 3 seconds, about 4 seconds, about 5 seconds, about 10 seconds, about 15 seconds, about 20 seconds, about 25 seconds, about 30 seconds, about 35 seconds, about 40 seconds, about 45 seconds, about 60 seconds, about 90 seconds, about 120 seconds, about 150 seconds, about 180 seconds, about 4 minutes, about 5 minutes, about 10 minutes, about 15 minutes, about 30 minutes, about 45 minutes, about 1 hour, about 90 minutes, or about 2 hours.

With continued reference to FIG. 1, the system 100 may include circuitry, networked processors, or the like configured to perform some or all of the processes described herein. For example, in some embodiments, the system 100 may include a controller 200 configured to receive data from the one or more online analyzers 150 (e.g., in electrical communication with the one or more online analyzers 150). FIG. 2 illustrates a schematic block diagram of example circuitry, some or all of which may be included in an example controller 200 that may be embodied by, at least partially embodied by, or may be commutatively connected to, an online analyzer 150 or any components thereof. However, it should be noted that the components, devices, and elements illustrated in and described with respect to FIG. 2 below may not be mandatory and thus some may be omitted in certain embodiments. Additionally, some embodiments may include further or different components, devices, or elements beyond those illustrated in and described with respect to FIG. 2.

In some embodiments, the controller 200 may be implemented as, or at least partially as, a distributed system or cloud based system and may therefore include any number of remote server devices. Accordingly, example embodiments of the controller 200 may employ remote processing and/or monitoring of data collected by the online analyzer(s) such that processing of such data may be performed on servers and/or other like computing devices. Regardless of implementation, controller 200 may be configured to control various components of the system as described herein (e.g., determine one or more additives and an amount of each additive to be added and add the at least one additive to the product stream).

Continuing with FIG. 2, controller 200 may be configured to perform actions in accordance with one or more example embodiments disclosed herein. In this regard, the controller 200 may be configured to perform and/or control performance of one or more functionalities of the system and/or components thereof in accordance with various example embodiments. For example, the controller 200 may be in communication with or otherwise control the one or more online analyzers 150 (e.g., to perform a reading or analysis) and/or other components of the apparatus (e.g., control one or more mechanisms to add the determined additive(s) to the product stream). The controller 200 may be further configured to perform data processing, such as processing of data collected by the online analyzer(s) 150. In some embodiments, controller 200, or a component(s) thereof, may be embodied as or comprise a circuit chip (e.g., an integrated circuit chip) configured (e.g., with hardware, software, or a combination of hardware and software) to perform operations described herein. The circuit chip may constitute various means, such as memory 201, processor 202, input/output circuitry 203, and/or communications circuitry 204, for performing one or more operations for providing the functionalities described herein. For example, a controller 200 may be configured, using one or more of the circuitry 201, 202, 203, and 204, to execute the operations described below in connection with FIG. 5.

Although the use of the term "circuitry" as used herein with respect to components 201-204 are described in some cases using functional language, it should be understood that the particular implementations necessarily include the use of particular hardware configured to perform the functions associated with the respective circuitry as described herein. It should also be understood that certain of these components 201-204 may include similar or common hardware. For example, two sets of circuitry may both leverage use of the same processor, network interface, storage medium, or the like to perform their associated functions, such that duplicate hardware is not required for each set of circuitry. It will be understood in this regard that some of the components described in connection with the controller 200 may be housed within this device, while other components are housed within another of these devices, or by yet another device not expressly illustrated.

While the term "circuitry" should be understood broadly to include hardware, in some embodiments, the term "circuitry" also includes software for configuring the hardware. For example, in some embodiments, "circuitry" may include processing circuitry, storage media, network interfaces, input/output devices, and the like. In some embodiments, other elements of the controller 200 may provide or supplement the functionality of particular circuitry. For example, the processor 202 may provide processing functionality, the memory 201 may provide storage functionality, the communications circuitry 204 may provide network interface functionality, and the like.

In some embodiments, the processor 202 (and/or coprocessor or any other processing circuitry assisting or otherwise associated with the processor) may be in communication with the memory 201 via a bus for passing information among components of, for example, controller 200. The memory 201 is non-transitory and may include, for example, one or more volatile and/or non-volatile memories, or some combination thereof. In other words, for example, the memory 201 may be an electronic storage device (e.g., a non-transitory computer readable storage medium). The memory 201 may be configured to store information, data, content, signals, applications, instructions (e.g., computer-executable program code instructions), or the like, for enabling a controller 200 to carry out various functions in accordance with example embodiments of the present disclosure. For example, memory 201 may be configured to store sensor data and/or any other suitable data or data structures. It will be understood that the memory 201 may be configured to store partially or wholly any electronic information, data, data structures, embodiments, examples, figures, processes, operations, techniques, algorithms, instructions, systems, apparatuses, methods, or computer program products described herein, or any combination thereof.

Although illustrated in FIG. 2 as a single memory, memory 201 may comprise a plurality of memory components. The plurality of memory components may be embodied on a single computing device or distributed across a plurality of computing devices. In various embodiments, memory 201 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 201 may be configured to store information, data, applications, instructions, or the like for enabling controller 200 to carry out various functions in accordance with example embodiments discussed herein. For example, in at least some embodiments, memory 201 is configured to buffer data for processing by processor 202. Additionally or alternatively, in at least some embodiments, memory 201 is configured to store program instructions for execution by processor 202. Memory 201 may store information in the form of static and/or dynamic information. This stored information may be stored and/or used by controller 200 during the course of performing its functionalities.

Processor 202 may be embodied in a number of different ways and may, for example, include one or more processing devices configured to perform independently. Additionally, or alternatively, processor 202 may include one or more processors configured in tandem via a bus to enable independent execution of instructions, pipelining, and/or multi-threading. Processor 202 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. The use of the term "processing circuitry" may be understood to include a single core processor, a multi-core processor, multiple processors internal to the controller 200, and/or remote or "cloud" processors. Accordingly, although illustrated in FIG. 3 as a single processor, it will be appreciated that in some embodiments, processor 202 comprises a plurality of processors. The plurality of processors may be embodied on a single computing device or may be distributed across a plurality of such devices collectively configured to function as controller 200. The plurality of processors may be in operative communication with each other and may be collectively configured to perform one or more functionalities of controller 200 as described herein. For example, some operations performed herein may be performed by components of the controller 200 while some operations may be performed on a remote device communicatively connected to the controller 200. For example, a user device such as a smart phone, tablet, personal computer and/or the like may be configured to communicate with the controller 200 such as by Bluetooth™ communication or over a local area network. Additionally or alternatively, a remote server device may perform some of the operations described herein, such as processing data collected by any of the sensors, and providing or communicating resultant data to other devices accordingly.

In an example embodiment, processor 202 is configured to execute instructions stored in the memory 201 or otherwise accessible to processor 202. Alternatively, or additionally, the processor 202 may be configured to execute hard-coded functionality. As such, whether configured by hardware or software methods, or by a combination thereof, the processor 202 may represent an entity (e.g., physically embodied in circuitry) capable of performing operations according to an embodiment of the present disclosure while configured accordingly. Thus, for example, when the processor 202 is embodied as an ASIC, FPGA, or the like, the processor 202 may be specifically configured hardware for conducting the operations described herein. Alternatively, as another example, when the processor 202 is embodied as an executor of software instructions, the instructions may specifically configure processor 202 to perform one or more algorithms and/or operations described herein when the instructions are executed. For example, these instructions, when executed by processor 202, may cause controller 200 to perform one or more of the functionalities of controller 200 as described herein.

In some embodiments, controller 200 further includes input/output circuitry 203 that may, in turn, be in communication with processor 202 to provide an audible, visual, mechanical, or other output and/or, in some embodiments, to receive an indication of an input from a user or another source. In that sense, input/output circuitry 203 may include means for performing analog-to-digital and/or digital-to-analog data conversions. Input/output circuitry 203 may include support, for example, for a display, touchscreen, keyboard, button, click wheel, mouse, joystick, an image capturing device (e.g., a camera), motion sensor (e.g., accelerometer and/or gyroscope), microphone, audio recorder, speaker, biometric scanner, and/or other input/output mechanisms. Input/output circuitry 203 may comprise a user interface and may comprise a web user interface, a mobile application, a kiosk, or the like. The processor 202 and/or user interface circuitry comprising the processor 202 may be configured to control one or more functions of a display or one or more user interface elements through computer program instructions (e.g., software and/or firmware) stored on a memory accessible to the processor 202 (e.g., memory 201, and/or the like). In some embodiments, aspects of input/output circuitry 203 may be reduced or may even be eliminated from controller 200. Input/output circuitry 203 may be in communication with memory 201, communications circuitry 204, and/or any other component(s), such as via a bus. Although more than one input/output circuitry 203 and/or other component can be included in controller 200, only one is shown in FIG. 3 to avoid overcomplicating the disclosure (e.g., like the other components discussed herein).

Communications circuitry 204, in some embodiments, includes any means, such as a device or circuitry embodied in either hardware, software, firmware or a combination of hardware, software, and/or firmware, that is configured to receive and/or transmit data from/to a network and/or any other device, circuitry, or module in communication with controller 200. In this regard, communications circuitry 204 may include, for example, a network interface for enabling communications with a wired or wireless communication network. Accordingly, the communications circuitry 204 may, for example, include supporting hardware and/or software for enabling wireless and/or wireline communications via cable, digital subscriber line (DSL), universal serial bus (USB), Ethernet, or other methods.

In some embodiments, the communications circuitry 204 may include a network configured to transmit information amongst various devices. By way of example, the communications circuitry 204 may be configured to enable communication amongst components of the system 100, the online analyzer(s) 150, and/or remote computing devices. In some embodiments, communications circuitry 204 is configured to receive and/or transmit any data that may be stored by memory 201 using any protocol that may be used for communications between computing devices. For example, communications circuitry 204 may include one or more network interface cards, antennae, transmitters, receivers, buses, switches, routers, modems, and supporting hardware and/or software, and/or firmware/software, or any other device suitable for enabling communications via a network. Additionally or alternatively, in some embodiments, communications circuitry 204 includes circuitry for interacting with the antenna(s) to cause transmission of signals via the antenna (e) or to handle receipt of signals received via the antenna (e). These signals may be transmitted by controller 200 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols. The network in which controller 200 and/or any of the components thereof may operate may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like). Communications circuitry 204 may additionally or alternatively be in communication with the memory 201, input/output circuitry 203 and/or any other component of controller 200, such as via a bus.

Example Methods

Referring to FIGS. 3-5, example methods of converting bioethanol to renewable jet fuel and for operating the systems 100 described herein are illustrated. That is, FIGS. 3-5 illustrate flowcharts containing series of steps for conducting an example bioethanol to renewable jet fuel conversion, for example, with the system 100 as described above.

The Dehydration Steps

Although it is contemplated that the dehydration step may be conducted in batch operation, it is preferred that the dehydration reaction is carried out as a substantially continuous operation. While it is contemplated that the dehydration reaction may be conducted in a single reaction vessel, these reaction steps may comprise two or more reactors or reaction stages in parallel, in series, or both, or any combination of reactor designs.

The dehydration reaction conditions are preferably controlled in the reaction in order to achieve the desired conversion and/or selectivity in accordance with the present disclosure. By way of example, but not by way of limitation, controlling or regulating any one or more of the following process parameters may achieve the desired conversion and/or selectivity: the temperature of the reaction, the flow rate of the reactants (e.g., incoming process stream), the presence of a dehydration catalyst, the amount of catalyst present in the reaction vessel, the shape and size of the reaction vessel, the pressure of the reaction, and any combination(s) of these and other process parameters which will be available and known to those skilled in the art in view of the disclosure contained herein.

In some example embodiments, example method 300 comprises providing bioethanol to a dehydration reaction zone as depicted in step 305. For example, bioethanol refined and processed from any one or more feedstock supplies (e.g., corn, grains, sugar cane, etc.) may be fed into a dehydration reaction zone (e.g., dehydration reaction zone 101 of a reactor of system 100).

With continued reference to FIG. 3, example method 300 comprises dehydrating at least a portion of the bioethanol to produce an ethylene process stream comprising ethylene as depicted in step 310. For example, in some embodiments, bioethanol ($C_2H_5OH$) may be converted to ethylene ($C_2H_4$) via step 310. The bioethanol provided in step 305 may contain a substantial amount of water (e.g., almost 40%) and it may be necessary to reduce the amount of such water in order to efficiently and ultimately convert the bioethanol to renewable jet fuel.

In some embodiments, step 310 is performed in the presence of a dehydration catalyst. For example, the dehydration catalyst may include, but is not limited to, gamma alumina, gamma alumina chelated with citric acid, mixture of gamma alumina and lanthanum trioxide, or combinations thereof. In certain embodiments, the dehydration catalyst is gamma alumina. The dehydration catalyst may be selected to improve the selectivity and/or performance of the dehydration steps.

The Oligomerization Steps

Although it is contemplated that the oligomerization steps may be conducted in batch operation, it is preferred that the oligomerization reaction is carried out as a substantially continuous operation. While it is contemplated that the oligomerization reaction may be conducted in a single reaction vessel, these reaction steps may comprise two or more reactors or reaction stages in parallel, in series, or both, or any combination of reactor designs.

The oligomerization reaction conditions are preferably controlled in the reaction in order to achieve the desired conversion and/or selectivity in accordance with the present disclosure. For example, the inventors have determined it may be undesirable to include a separate dimerization step prior to such oligomerization steps (e.g., dimerize ethylene to butylene ($C_4H_8$) and then subject such butylene to oligomerization) and may selectively utilize an oligomerization catalyst such that either dimerization is not required or very minimal dimerization occurs, for example, in a single reactor system. Moreover, by way of example, but not by way of limitation, controlling or regulating any one or more of the following process parameters may achieve the desired conversion and/or selectivity: the temperature of the reaction, the flow rate of the reactants (e.g., incoming process stream), the flow rate of unconverted C9-olefins recycle, the presence of an oligomerization catalyst, the amount of catalyst present in the reaction vessel, the shape and size of the reaction vessel, the pressure of the reaction, and any combination(s) of these and other process parameters which will be available and known to those skilled in the art in view of the disclosure contained herein.

In some example embodiments, example method 400 comprises providing an ethylene process stream to an oligomerization reaction zone as depicted in step 405. For example, the ethylene formed in step 310 may be fed into an oligomerization reaction zone (e.g., oligomerization reaction zone 102 of a reactor of system 100).

With continued reference to FIG. 4, example method 400 comprises oligomerizing at least a portion of the ethylene process stream to produce an olefin process stream as depicted in step 410. In some embodiments, step 410 is performed in the presence of an oligomerization catalyst. For example, the oligomerization catalyst may include, but is not limited to, zeolite base solid acid catalysts with alumina/silica binders, such as ZSM 23, ZSM 24, and similar family, or combinations thereof.

Additionally or alternatively, method 400 may optionally include removing lighter olefins from the olefin process stream as depicted in step 415. For example, instead of allowing lighter olefins (e.g., having less than nine carbon atoms) from proceeding through the reactor(s) to the hydrogenation reaction zone (e.g., hydrogenation reaction zone 103), system 100 may be configured to identify and withdraw such lighter olefins from the olefin process stream. For example, in some embodiments, fractionation may be used to identify and/or separate lighter olefins. Removal of lighter olefins (e.g., olefins with less than nine carbon atoms) from the reactor system 100 may reduce operating costs and lead to improved efficiency.

Additionally or alternatively, in still further embodiments, example method 400 may optionally include recycling the removed lighter olefins back into the oligomerization reaction zone (e.g., oligomerization reaction zone 102) as depicted in step 420. Such recycling back into the oligomerization reaction zone 102 in order to further oligomerize such lighter olefins into jet fuel-compatible range may further maximize the conversion toward jet fuel-compatible hydrocarbons (e.g., predominantly C9-C14 jet range components).

The Hydrogenation Steps

In some example embodiments, the olefin process stream may be subjected to a mild hydrogenation process in order to reduce the olefinic components and produce saturated hydrocarbons. Although it is contemplated that the hydrogenation step may be conducted in batch operation, it is preferred that the hydrogenation reaction is carried out as a substantially continuous operation. While it is contemplated that the hydrogenation reaction may be conducted in a single reaction vessel, this reaction step may comprise two or more reactors or reaction stages in parallel, in series, or both, or any combination of reactor designs.

The hydrogenation reaction conditions are preferably controlled in the reaction in order to achieve the desired conversion and/or selectivity in accordance with the present disclosure. By way of example, but not by way of limitation, controlling or regulating any one or more of the following process parameters may achieve the desired conversion and/or selectivity: the temperature of the reaction, the flow rate of the reactants (e.g., incoming process stream), the presence of a hydrogenation catalyst, the amount of catalyst present in the reaction vessel, the shape and size of the reaction vessel, the pressure of the reaction, and any combination(s) of these and other process parameters which will be available and known to those skilled in the art in view of the disclosure contained herein.

With reference to FIG. 5, in one embodiment, example method 500 may include receiving the olefin process stream comprising olefins as depicted in step 505. For example, in some embodiments, the hydrogenation reaction zone (e.g., hydrogenation reaction zone 103) receives the olefin process stream from the oligomerization reaction zone (e.g., oligomerization reaction zone 102) as prepared in method 400. In some embodiments, the oligomerization reaction zone 102 may be disposed upstream of the hydrogenation reaction zone 103. In other embodiments, the oligomerization reaction zone 102 and the hydrogenation reaction zone 103 are the same reaction zone. In a preferred embodiment, the olefin process stream comprises a majority of longer carbon chain olefins (e.g., greater than nine carbon atoms).

With continued reference to FIG. 5, example method 500 comprises hydrogenating, in the hydrogenation reaction zone (e.g., hydrogenation reaction zone 103) at least a portion of the olefin process stream to produce a product stream comprising jet-range compatible hydrocarbons as depicted in step 510. For example, the longer carbon chain olefins as produced in the oligomerization reaction zone 102 as depicted in method 400 may be subjected to a mild hydrogenation process in order to reduce the olefinic components and produce high value saturated hydrocarbons (e.g., C9-C14 hydrocarbons). In some embodiments, step 510 is performed in the presence of a hydrogenation catalyst. For example, the hydrogenation catalyst may include, but is not limited to, metallic catalysts containing, e.g., palladium, rhodium, nickel, ruthenium, platinum, rhenium, cobalt, molybdenum, or combinations thereof, and the supported versions thereof, platinum (e.g., ranging 0.2 to 1 wt %) on alumina, amorphous silica alumina, nickel on alumina, and mixtures thereof, or combinations thereof. Such hydrogenation catalyst(s) may be selected to maximize isomerization and further increase an iso-to-normal ratio of the C9-C14 hydrocarbons in order to enhance cold flow properties of the SAF.

With continued reference to FIG. 5, example method 500 comprises determining an iso-to-normal ratio of a portion of the product stream via one or more online analyzers (e.g., online analyzer 150) in the hydrogenation reaction zone (e.g., hydrogenation reaction zone 103) as depicted in step 515. In some embodiments, the one or more online analyzers are configured to determine the iso-to-normal ratio of the portion of the product stream in real time. In still other embodiments, the one or more online analyzers comprise one or more sensors configured to continuously and/or intermittently monitor the iso-to-normal ratio of the product stream.

With continued reference to FIG. 5, example method 500 comprises, in an instance wherein the determined iso-to-normal ratio at step 515 fails to satisfy a predetermined iso-to-normal threshold ratio, determining at least one additive and an amount of the at least one additive to be added to the product stream as depicted in step 520. For example, the additives may include, but are not limited to, styrene, benzaldehyde, methyl benzoate, and acetophenone. In some embodiments, the predetermined iso-to-normal threshold ratio is correlated to a freeze point specification dictated by standards of industry. For example, in a certain embodiment, the predetermined iso-to-normal threshold ratio is correlated to a freeze point specification dictated by ASTM D7566. In some embodiments, the predetermined iso-to-normal threshold ratio is at least 14:1. In still further embodiments, the predetermined iso-to-normal threshold ratio is at least 15:1.

In an example embodiment, the online analyzer 150 may transmit the iso-to-normal ratio determined in step 515 to a controller 200 and the controller 200 may determine whether or not the determined iso-to-normal ratio at step 515 satisfies a predetermined iso-to-normal threshold ratio. For example, in some embodiments, the online analyzer 150 may be communicably coupled to the controller 200 and the controller 200 may have means (e.g., memory 201, processor 202, input/output circuitry 203, and/or communications circuitry 204) to determine which additive(s) and in what amount need to be added to the product stream.

Additionally or alternatively, in another example embodiment, the online analyzer 150 may calculate a predicted freeze point value based on the determined iso-to-normal ratio and transmit such predicted freeze point value to the controller 200. Because the additives are configured to adjust a freeze point of the product stream, the controller 200 may use such predicted freeze point value to determine the at least one additive and the amount of the at least one additive to be added to the product stream.

With continued reference to FIG. 5, example method 500 comprises adding the at least one additive to the product stream prior to the product stream exiting the hydrogenation reaction zone as depicted in step 525. The determination and addition of additives can be more controlled and costs reduced by adding to an active batch. Although not depicted, the resulting product stream may be optionally blended with conventional jet fuel.

Thus, particular embodiments of the subject matter have been described. While this specification contains many specific implementation details, these should not be construed as limitations on the scope of any inventions or of what may be claimed, but rather as description of features specific to particular embodiments of the disclosure. Other embodiments are within the scope of the following claims. Certain features that are described herein in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations or steps are depicted in the drawings in a particular order, this should not be understood as requiring that such operations or steps may be performed in the particular order shown or in sequential order, or that all illustrated operations or steps be performed, to achieve desirable results, unless described otherwise. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products. Any operational step shown in broken lines in one or more flow diagrams illustrated herein are optional for purposes of the depicted embodiment.

In some cases, the actions recited in the claims can be performed in a different order and still achieve desirable results. In addition, the processes depicted in the accompanying figures do not necessarily require the particular order shown, or sequential order, to achieve desirable results, unless described otherwise. In certain implementations, multitasking and parallel processing may be advantageous.

Overview of Terms

The following explanations of terms are provided to better describe the present disclosure and to guide those of ordinary skill in the art in the practice of the present disclosure.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the terms "illustrative," "example," "exemplary" and the like are used to mean "serving as an example, instance, or illustration" with no indication of quality level. Any implementation described herein as "exemplary" or "example" is not necessarily to be construed as preferred or advantageous over other implementations.

The terms "about," "approximately," "generally," "substantially," or the like, when used with a number, may mean that specific number, or alternatively, a range in proximity to the specific number, as understood by persons of skill in the art field and may be used to refer to within manufacturing and/or engineering design tolerances for the corresponding materials and/or elements as would be understood by the person of ordinary skill in the art, unless otherwise indicated.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

If the specification presents a list, unless stated otherwise, it is to be understood that each individual element of that list, and every combination of components of that list, is a separate embodiment. For example, "1, 2, 3, 4, and 5" encompasses, among numerous embodiments, 1; 2; 3; 1 and 2; 3 and 5; 1, 3, and 5; and 1, 2, 4, and 5.

The term "plurality" refers to two or more items.

The term "set" refers to a collection of one or more items.

The term "or" is used herein in both the alternative and conjunctive sense, unless otherwise indicated.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting, unless otherwise indicated. Other features of the disclosure are apparent from the detailed description and the claims.

While the present disclosure has been particularly described in conjunction with specific examples, it is evident that many alternatives, modifications, and variations will be apparent to those skilled in the art in light of the foregoing description. It is therefore contemplated that the appended claims will embrace any such alternatives, modifications, and variations as falling.

CONCLUSION

Many modifications and other embodiments of the present disclosure set forth herein will come to mind to one skilled in the art to which the present disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed:

1. A method for converting bioethanol to renewable jet fuel, the method comprising:
    hydrogenating, in a hydrogenation reaction zone, at least a portion of an olefin process stream comprising olefins to produce a product stream comprising jet-range compatible hydrocarbons, wherein the olefins are formed from bioethanol;
    determining, in the hydrogenation reaction zone, an iso-to-normal ratio of a portion of the product stream via one or more online analyzers;

in an instance wherein the determined iso-to-normal ratio fails to satisfy a predetermined iso-to-normal threshold ratio, determine at least one additive and an amount of the at least one additive to be added to the product stream, the at least one additive configured to adjust a freeze point of the product stream; and adding the at least one additive to the product stream prior to the product stream exiting the hydrogenation reaction zone.

2. The method according to claim 1, wherein at least one of the one or more online analyzers is configured to determine the iso-to-normal ratio of the portion of the product stream in real time.

3. The method according to claim 1, wherein the one or more online analyzers comprise one or more sensors configured to continuously and/or intermittently monitor the iso-to-normal ratio of the product stream.

4. The method according to claim 1, wherein the one or more online analyzers are configured to communicate with a controller, the controller configured to add the least one additive to the product stream.

5. The method according to claim 1, wherein the predetermined iso-to-normal threshold ratio is correlated to a freeze point specification dictated by ASTM D7566.

6. The method according to claim 1, wherein the predetermined iso-to-normal threshold ratio is at least 14:1.

7. The method according to claim 1, wherein the method further comprises:
providing bioethanol to a dehydration reaction zone; and
dehydrating at least a portion of the bioethanol to produce an ethylene process stream comprising ethylene.

8. The method according to claim 7, wherein dehydrating at least a portion of the bioethanol is performed in the presence of a dehydration catalyst.

9. The method according to claim 8, wherein the dehydration catalyst is gamma alumina.

10. The method according to claim 7, wherein the method further comprises:
providing the ethylene process stream to an oligomerization reaction zone; and
oligomerizing at least a portion of the ethylene process stream to produce the olefin process stream.

11. The method according to claim 10, the method further comprising:
removing lighter olefins having less than nine carbon atoms from the olefin process stream.

12. The method according to claim 11, the method further comprising:
recycling the removed lighter olefins back into the oligomerization reaction zone.

13. A system configured to convert bioethanol to renewable jet fuel, the system comprising:
a hydrogenation reaction zone configured to produce a product stream comprising jet-range compatible hydrocarbons;

one or more online analyzers, wherein each online analyzer is configured to determine an iso-to-normal ratio of a portion of the product stream in the hydrogenation reaction zone; and a controller communicably coupled to the one or more online analyzers, wherein the controller is configured to:
in an instance wherein the determined iso-to-normal ratio fails to satisfy a predetermined iso-to-normal threshold ratio, determine at least one additive and an amount of the at least one additive to be added to the product stream, the at least one additive configured to adjust a freeze point of the product stream, and
add the at least one additive to the product stream prior to the product stream exiting the hydrogenation reaction zone.

14. The system of claim 13, wherein the predetermined iso-to-normal threshold ratio is at least 14:1.

15. The system of claim 13, wherein the hydrogenation reaction zone is configured to:
receive an olefin process stream comprising olefins; and
hydrogenate at least a portion of the olefin process stream to produce the product stream comprising jet-range compatible hydrocarbons.

16. The system of claim 15, wherein the system further comprises a dehydration reaction zone disposed upstream of the hydrogenation reaction zone, the dehydration reaction zone configured to:
receive a starting material stream comprising bioethanol; and
dehydrate, in the presence of a dehydration catalyst, at least a portion of the starting material stream to produce an ethylene process stream comprising ethylene.

17. The system of claim 16, wherein the system further comprises an oligomerization reaction zone disposed upstream of the hydrogenation reaction zone and downstream of the dehydration reaction zone, the oligomerization reaction zone configured to:
receive the ethylene process stream; and
oligomerize, in the presence of an oligomerization catalyst, at least a portion of the ethylene process stream to produce the olefin process stream.

18. The system of claim 17, wherein the system is configured to remove at least a portion of lighter olefins from the olefin process stream, the lighter olefins having less than nine carbon atoms.

19. The system of claim 18, wherein the system is configured to recycle the removed lighter olefins back into the oligomerization reaction zone.

20. The system of claim 13, wherein the one or more online analyzers each comprise one or more sensors configured to continuously and/or intermittently monitor the iso-to-normal ratio of the product stream.

* * * * *